US008568846B2

(12) United States Patent
Dakka et al.

(10) Patent No.: US 8,568,846 B2
(45) Date of Patent: Oct. 29, 2013

(54) PROCESS FOR MAKING POLYOL NEOALKYLESTER PLASTICIZERS FROM NEO ACIDS

(75) Inventors: Jihad Mohammed Dakka, Whitehouse Station, NJ (US); Edmund John Mozeleski, Califon, NJ (US); Lisa Saunders Baugh, Ringoes, NJ (US); Jon Edmond Randolph Stanat, Houston, TX (US); Karla Schall Colle, Magnolia, TX (US); Francisco Manuel Benitez, Houston, TX (US); Peter Stokes James, Katy, TX (US); Allen David Godwin, Seabrook, TX (US); Carl Robert Beck, Baton Rouge, LA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 434 days.

(21) Appl. No.: 12/880,586

(22) Filed: Sep. 13, 2010

(65) Prior Publication Data

US 2011/0165355 A1    Jul. 7, 2011

Related U.S. Application Data

(60) Provisional application No. 61/284,838, filed on Dec. 24, 2009.

(51) Int. Cl.
*B32B 1/08* (2006.01)
*C08K 5/10* (2006.01)

(52) U.S. Cl.
USPC .......... 428/36.9; 524/311; 524/312; 524/287; 524/385; 524/313; 554/227; 554/128; 554/124

(58) Field of Classification Search
USPC ......... 428/36.9; 524/311, 312, 313, 287, 385; 554/227, 128, 124
See application file for complete search history.

(56) References Cited

U.S. PATENT DOCUMENTS

| | | | |
|---|---|---|---|
| 5,248,531 A | 9/1993 | Nagai et al. | |
| 6,652,774 B2 | 11/2003 | Zhou et al. | |
| 6,734,241 B1 | 5/2004 | Nielsen et al. | |
| 6,740,254 B2 | 5/2004 | Zhou et al. | |
| 6,777,514 B2 | 8/2004 | Patil et al. | |
| 6,811,722 B2 | 11/2004 | Zhou et al. | |
| 7,145,049 B2 | 12/2006 | Loescher et al. | |
| 7,253,330 B2 | 8/2007 | Dakka et al. | |
| 7,297,738 B2 | 11/2007 | Gosse et al. | |
| 7,507,868 B2 | 3/2009 | Duncan et al. | |
| 8,163,825 B2 * | 4/2012 | Colle et al. | 524/312 |
| 2005/0014630 A1 | 1/2005 | Dakka et al. | |
| 2006/0247461 A1 | 11/2006 | Schlosberg et al. | |
| 2008/0242895 A1 | 10/2008 | Godwin et al. | |

FOREIGN PATENT DOCUMENTS

| | | |
|---|---|---|
| WO | 9932427 | 7/1999 |
| WO | 03029339 | 4/2003 |
| WO | 03082778 | 10/2003 |
| WO | 03082781 | 10/2003 |
| WO | 2004046078 | 6/2004 |

OTHER PUBLICATIONS

Co-pending U.S. Appl. No. 61/040,480, filed Mar. 28, 2008.
Copending U.S. Appl. No. 61/211,279, filed Mar. 27, 2009.
Copending U.S. Appl. No. 61/279,671, filed Oct. 23, 2009.
Godwin, A.D., "Plasticizers", Applied Polymer Science 21st Century, edited by C.D. Craver and C.E. Carraher, Elsevier (2000), pp. 157-175.
P.A. Small, "Some Factors Affecting the Solubility of Polymers", J. Appl. Chem., 3, pp. 76-80 (1953).

\* cited by examiner

*Primary Examiner* — Robert D. Harlan
(74) *Attorney, Agent, or Firm* — Robert A. Migliorini

(57) ABSTRACT

Provided are compositions, processes for making, and processes for using neoalkyl polyol esters and triglycerides as plasticizers. In one form, a neoalkylester triglyceride plasticizers can be produced by (i) drying a polyol feedstream; (ii) contacting in a reactor the dried polyol feedstream with a neoacid feedstream under effective temperature, pressure and time to form a neoalkylester plasticizer effluent stream, and (iii) purifying the neoalkylester plasticizer effluent stream to remove unreacted polyol and unreacted neoacid to form a neoalkylester plasticizer. Such plasticizers can be phthalate-free and provide outstanding properties including a suitable melting or pour point, glass transition temperature, low volatility, increased compatibility, increased hydrolytic stability, and excellent low temperature properties in a range of polymeric resins.

34 Claims, 5 Drawing Sheets

PROCESS FOR MAKING POLYOL NEOALKYLESTER PLASTICIZERS FROM NEO ACIDS

CROSS-REFERENCE TO RELATED APPLICATION

This is a Non-Provisional Application that claims priority to U.S. Provisional Application No. 61/284,838 filed on Dec. 24, 2009 and herein incorporated by reference in its entirety.

FIELD

The present disclosure relates to a process for making polyol neoalkylester plasticizers from neo acids.

BACKGROUND

Plasticizers are incorporated into a resin (usually a plastic or elastomer) to increase the flexibility, workability, or distensibility of the resin. The largest use of plasticizers is in the production of "plasticized" or flexible polyvinyl chloride (PVC) products. Typical uses of plasticized PVC include films, sheets, tubing, coated fabrics, wire and cable insulation and jacketing, toys, flooring materials such as vinyl sheet flooring or vinyl floor tiles, adhesives, sealants, inks, and medical products such as blood bags and tubing, and the like.

Other polymer systems that use small amounts of plasticizers include polyvinyl butyral, acrylic polymers, poly(vinylidene chloride), nylon, polyolefins, polyurethanes, and certain fluoroplastics. Plasticizers can also be used with rubber (although often these materials fall under the definition of extenders for rubber rather than plasticizers). A listing of the major plasticizers and their compatibilities with different polymer systems is provided in "Plasticizers," A. D. Godwin, in Applied Polymer Science 21st Century, edited by C. D. Craver and C. E. Carraher, Elsevier (2000); pp. 157-175.

Plasticizers can be characterized on the basis of their chemical structure. The most important chemical class of plasticizers is phthalic acid esters, which accounted for about 85% worldwide of PVC plasticizer usage in 2002. However, in the recent past there as been an effort to decrease the use of phthalate esters as plasticizers in PVC, particularly in end uses where the product contacts food, such as bottle cap liners and sealants, medical and food films, or for medical examination gloves, blood bags, and IV delivery systems, flexible tubing, or for toys, and the like. For these and most other uses of plasticized polymer systems, however, a successful substitute for phthalate esters has heretofore not materialized.

One such suggested substitute for phthalates are esters based on cyclohexanoic acid. In the late 1990's and early 2000's, various compositions based on cyclohexanoate, cyclohexanedioates, and cyclohexanepolyoate esters were said to be useful for a range of goods from semi-rigid to highly flexible materials. See, for instance, WO 99/32427, WO 2004/046078, WO 2003/029339, WO 2004/046078, U.S. Application No. 2006-0247461, and U.S. Pat. No. 7,297,738.

Other suggested substitutes include esters based on benzoic acid (see, for instance, U.S. Pat. No. 6,740,254, and also co-pending, commonly-assigned, U.S. Patent Application Ser. No. 61/040,480, filed on Mar. 28, 2008 and polyketones, such as described in U.S. Pat. No. 6,777,514; and also co-pending, commonly-assigned, U.S. patent application Ser. No. 12/058,397 filed on Mar. 28, 2008. Epoxidized soybean oil, which has much longer alkyl groups ($C_{16}$ to $C_{18}$) has been tried as a plasticizer, but is generally used as a PVC stabilizer. Stabilizers are used in much lower concentrations than plasticizers.

Typically, the best that has been achieved with substitution of the phthalate ester with an alternative material is a flexible PVC article having either reduced performance or poorer processability. Thus, heretofore efforts to make phthalate-free plasticizer systems for PVC have not proven to be entirely satisfactory, and this is still an area of intense research.

Plasticizers based on triglycerides have been tried in the past, but they have mostly been based on natural triglycerides from various vegetable oils. The alkyl groups on these natural triglycerides are linear, and can cause compatibility problems when the alkyl chain is too long.

"Structural Expressions of Long-Chain Esters on Their Plasticizing Behavior in Poly(Vinyl Chloride)", H. K. Shobha and K. Kishore, Macromolecules 1992, 25, 6765-6769, reported the influence of branching and molecular weight in long-chain esters in PVC. Triglycerides (TGE's) having linear alkyl groups were studied.

"Method for Determining Compatibility Parameters of Plasticizers for Use in PVC Through Use of Torsional Modulus", G. R. Riser and W. E. Palm, Polymer Engineering and Science, April 1967, 110-114, also investigate the use of triglycerides and their plasticizing behavior with PVC, including tri-iso-valerin (3-methyl butanoate) triglyceride. It was reported that "these materials have volatilities that are much too high for good long-time permanence".

Nagai et al. in U.S. Pat. No. 5,248,531, teaches the use of articles comprising vinyl chloride-type resins (among others) using triglyceride compounds as a hemolysis depressant, and also comprising 10 to 45 wt % of plasticizers selected from trialkyl trimellitates, di-normal alkyl phthalates, and tetraalkyl pyromellitates. The alkyl chains of the acid-derived moiety $R^1$-$R^3$ in the structure below, formula (I), are independently an aliphatic hydrocarbon group of 1 to 20 carbon atoms and in embodiments at least one of the alkyl chains is branched. One specific triglyceride disclosed is glyceryl tri-2-ethylhexanoate.

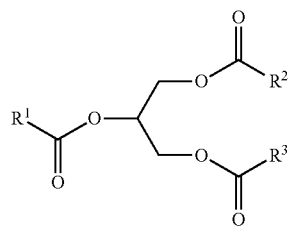

I

Zhou et al. discloses, in U.S. Pat. Nos. 6,652,774; 6,740,254; and 6,811,722; phthalate-free plasticizers comprising a mixture of different triesters of glycerin, preferably wherein the phthalate-free plasticizer is formed by a process of esterifying glycerin with a mixture comprising a mixture of alkyl acids and aryl acids. Zhou et al. also discloses that glyceryl tribenzoate and glyceryl tri(2-ethyl)hexanoate have not been used as primary plasticizers in vinyl polymers, such as PVC because they are known to be incompatible with such resins.

Nielsen et al., in U.S. Pat. No. 6,734,241, teach a composition comprising a thermoplastic polymer as in formula (I) above, wherein at least one of the R groups is an alkyl group having from 1-5 carbon atoms and at least one of the R groups is a saturated branched alkyl group having from 9 to 19 carbon atoms and a hydrophilic group.

Among the problems presented by the aforementioned triglycerides is they cannot be made conveniently and thus generally are quite expensive and/or are specialty chemicals not suitable as replacements for phthalates from an economic standpoint and/or are not as compatible with the range of polymer systems that phthalates are compatible with, and thus are not viable replacements for phthalates from a physical property standpoint.

For instance, some synthesis methods involve at least two separate steps, such as where the glycerol is first partially esterified with the $C_{10}$ to $C_{20}$ branched chain acyl halide, and then reacted with acetic acid or acetic anhydride to provide the remaining groups.

Other syntheses involving mixed acid feeds will require addition of a hydrocarbon solvent for azeotropic distillation of the water to drive the esterification reaction to completion (as measured by the hydroxyl number of the ester, which is a measure of the amount of unreacted OH groups), due to the spread in boiling points between the mixed acids. In addition, the use of mixed acid feedstock such as cited in Zhou et al. and in Nielsen et al. can reduce the capability of recycling unreacted acids.

Triglycerides based on acids derived from natural products will be limited to naturally occurring linear alkyl groups with even carbon numbers, which offer very little flexibility in designing an appropriate plasticizer system for a given polymer system.

Thus what is needed is a method of making a general purpose non-phthalate plasticizer providing a plasticizer having suitable melting or pour point, glass transition temperature, increased compatibility, good performance and low temperature properties.

Triglycerides produced by esterification of glycerol with a combination of acids derived from the hydroformylation and subsequent oxidation of $C_3$ to $C_{12}$ olefins provide for triglycerides having excellent compatibility with a wide variety of resins. Esterification of glycerol using a combination of these acids eliminates many of the aforementioned problems, and enables high yields of the glycerol triesters to be obtained, which have excellent compatibility with vinyl polymers. These acids are generally alkyl acids that are linear, branched or a combination thereof. However, it is generally recognized in the art that plasticizers produced from linear or branched alkyl acids have poor chemical stability toward hydrolysis. Alkyl triglycerides exhibit non-optimal stability towards hydrolysis over time of the internal (secondary) ester moiety. As a result, they have a higher volatility and lower permanence in PVC formulations due to the presence of hydrolysis products (diesters; free acids) in the formulation.

Hence, there is a need for a process to produce polyol alkylester plasticizers having improved hydrolytic stability, and for plasticized polymer compositions containing these more hydrolytically stable alkylester plasticizers.

SUMMARY

The present disclosure is directed to a process for producing a neoalkylester plasticizer comprising: (i) drying a polyol feedstream; (ii) contacting the dried polyol feedstream with a CO recycle inerts purge stream to absorb $BF_3$; (iii) pressurizing to 1500 to 2500 psig the contacted dried polyol feedstream, a branched olefin feedstream and a CO feedstream; (iv) combining the pressurized contacted dried polyol feedstream, the branched olefin feed stream and the CO feedstream in a reactor; (v) maintaining the reactor at a temperature of 20 to 80° C. for an effective amount of time to form a reactor effluent stream; (vi) flashing off $BF_3$ and unreacted CO from the reactor effluent stream after the reactor to form a flashed reactor effluent stream; (vii) heating the flashed reactor effluent stream to remove unreacted branched olefin to form a crude neoalkylester plasticizer; and (viii) removing residual polyol, oligomers or other impurities from the crude neoester plasticizer to form a neoalkylester plasticizer.

The present disclosure is also directed to a plasticizer comprising a triglyceride according to the formula:

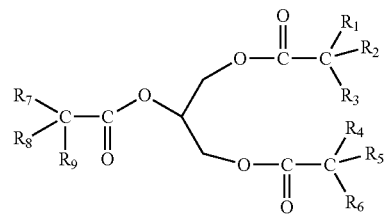

wherein the sum of the carbons for the neoalkyl ester groups ($R^1$, $R^2$, $R^3$, $R^4$, $R^5$, $R^6$, $R^7$, $R^8$, $R^9$, plus the three carbons for the quaternary carbons bearing $R^1$-$R^9$, plus the three carbons for the three carbonyl groups, and not including the three glycerol backbone carbons) ranges from 20 to 25; and wherein the neoalkyl ester groups ($—C(R^1)(R^2)(R^3)$, $—C(R^4)(R^5)(R^6)$, and $—C(R^7)(R^8)(R^9)$ groups) comprise $C_4$ to $C_{12}$ neoalkyl groups.

The present disclosure is also directed to a process for producing a neoalkylester plasticizer comprising: (i) contacting a crude glycerol or purified polyol feedstream with a neoacid feedstream in a reactor under effective temperature, pressure and time to form a neoalkylester plasticizer effluent stream, and (ii) purifying the neoalkylester plasticizer effluent stream to remove unreacted polyol, unreacted neoacid, and other impurities to form a neoalkylester plasticizer.

The present disclosure is still further directed to process for producing a neoalkylester plasticizer comprising: (i) drying a polyol feedstream; (ii) contacting in a reactor the dried polyol feedstream with a neoacid feedstream under effective temperature, pressure and time to form a neoalkylester plasticizer effluent stream, and (iii) purifying the neoalkylester plasticizer effluent stream to remove unreacted polyol and unreacted neoacid to form a neoalkylester plasticizer.

The present disclosure is still further directed to a plasticizer comprising a triglyceride according to the formula

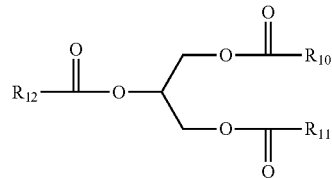

wherein $R_{10}$, $R_{11}$ and $R_{12}$ comprise an aryl group, neoalkyl group or combinations thereof, wherein the sum of the carbons for the aryl or neoalkyl groups plus the three carbons for the three carbonyl groups, and not including the three glycerol backbone carbons ranges from 20 to 25; and wherein the branching of the neoalkyl groups is from 2.0 to 3.0 branches per group.

The present disclosure is still further directed to resin compositions, plastisols and articles comprising the above plasticizer compositions to provide phthalate-free plasticizers, resin compositions, plastisols and articles.

These and other objects, features, and advantages will become apparent as reference is made to the following detailed description, embodiments, examples, and appended claims.

BRIEF DESCRIPTION OF THE DRAWINGS

In the accompanying drawings, like reference numerals are used to denote like parts throughout the several views.

DETAILED DESCRIPTION

Figure 1:
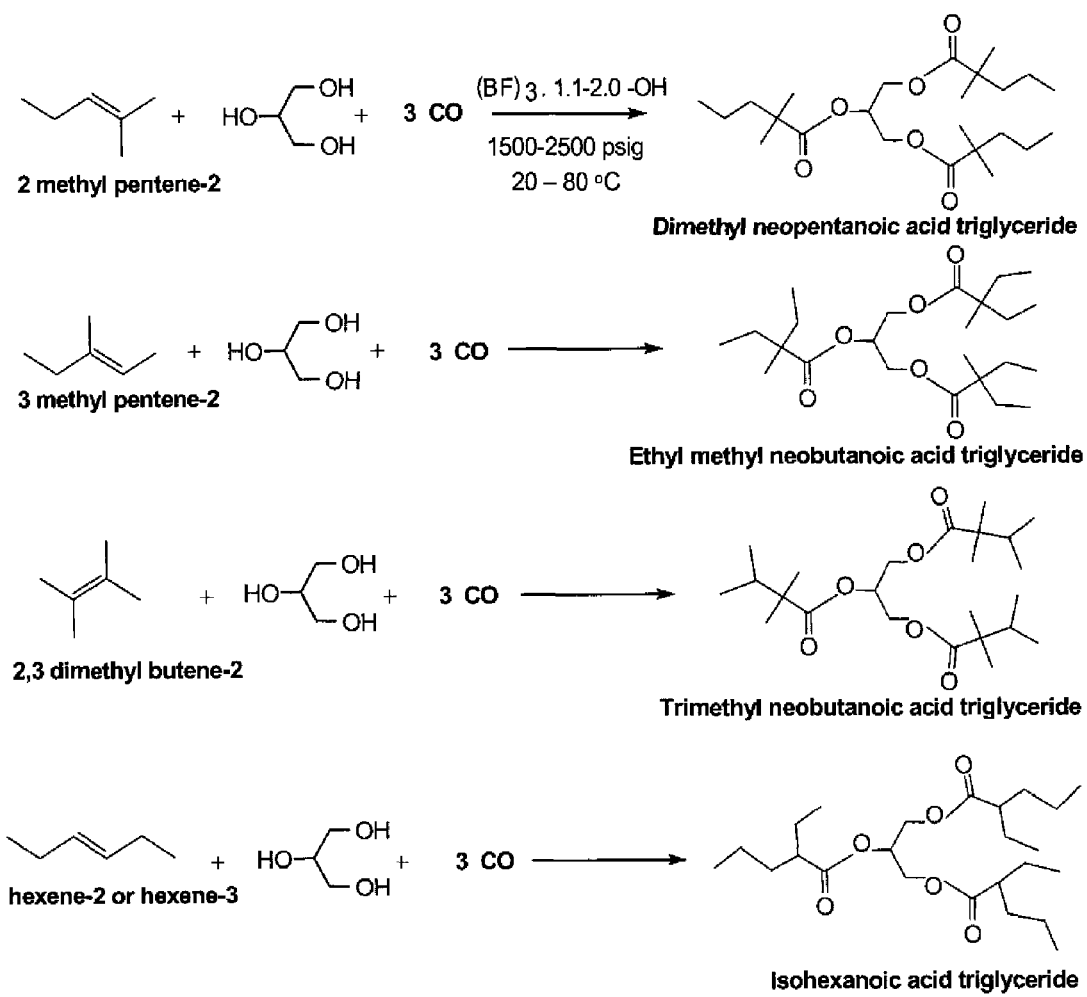
FIG. 1 is a depiction of the Koch glycerol direct esterification chemistry of the present disclosure.

All numerical values within the detailed description and the claims herein are modified by "about" or "approximately" the indicated value, and take into account experimental error and variations that would be expected by a person having ordinary skill in the art.

Neo acids are carboxylic acids in which the carbon alpha to the C=O group is a quaternary carbon, i.e., a carbon that bears three non-hydrogen alkyl substituents of methyl ($C_1$) or greater size. It has been discovered that the use of neo sidechains provide greater hydrolytic stability in alkyl esters, and therefore present an advantage for use as plasticizers. In particular, polyol neoalkylester plasticizers and methods of making such plasticizers via esterification of a neo acid with a polyol yields plasticizers with improved hydrolytic stability compared to linear and other branched alkylester plasticizers.

U.S. Provisional Application No. 61/203,626 filed on Dec. 24, 2008, herein incorporated by reference in its entirety, discloses mixed triglyceride compositions, processes for making, and processes for using triglycerides as plasticizers. In one form of the process for making such mixed triglycerides, the steps include (i) recovering at least one linear $C_4$ to $C_{13}$ aldehyde, one branched $C_4$ to $C_{13}$ aldehyde, or a combination thereof from a hydroformylation product; (ii) oxidizing the linear, branched or combination thereof $C_4$ to $C_{13}$ aldehyde to form a linear, branched or combination thereof $C_4$ to $C_{13}$ acid; (iii) esterifying the linear, branched or combination thereof $C_4$ to $C_{13}$ acid with a polyol to yield a linear alkyl triglyceride, a branched alkyl triglyceride, or a combination thereof; and (iv) purifying the linear, branched or combination thereof alkyl triglyceride to form a plasticizer, wherein the total carbon number of the triester groups ranges from 20 to 25 for greater than or equal to 45 wt % of the plasticizer. Pure glycerol is one of polyols that may be used in esterfying the linear, branched or combination thereof $C_4$ to $C_{13}$ acid to yield a linear alkyl triglyceride, a branched alkyl triglyceride, or a combination thereof.

U.S. Provisional Application No. 61/211,279, filed on Mar. 27, 2009, herein incorporated by reference in its entirety, discloses methods of making mixed triglycerides using crude glycerol for use as plasticizers for polymer resins.

U.S. Provisional Application No. 61/279,671, filed on Oct. 23, 2009, herein incorporated by reference in its entirety, discloses triglyceride plasticizers produced by recovery of linear or branched $C_4$ to $C_{13}$ aldehydes from a hydroformylation product, oxidation to linear or branched $C_4$ to $C_{13}$ acids with oxygen and/or air, recovery of the resulting acids, combining the linear or branched $C_4$ to $C_{13}$ acids with benzoic acid, toluic acid or a combination thereof to form a mixed acid blend, and esterification of the mixed acid blend with glycerol, wherein the total carbon number of the triester groups ranges from 20 to 25 and includes from 1 to 2 aryl groups for greater than or equal to 45 wt % of the plasticizer.

With regard to the present disclosure, the applicants have surprisingly discovered that polyol neoalkylesters yield improved hydrolytic stability, and therefore are advantageous for use as plasticizers.

One potential route to non-phthalate plasticizers is to produce a polyol neoalkylester. The polyol neoalkylester could be made from the direct esterification of a neo acid with a polyol. Neo acids are made from branched olefins, carbon monoxide and water or alcohol using Koch chemistry.

Alternately, the polyol neoalkylester could be made from branched olefins, carbon monoxide, and a polyol via direct esterification using a variant of Koch chemistry. This variant of Koch chemistry can be executed by first forming a $BF_3$-polyol complex using a stoichiometric ratio of between 0.5 and 2.5 $BF_3$ molecules per hydroxyl group on the polyol, then adding a molar excess of carbon monoxide, and then adding olefins. The reaction can be carried out at temperatures between 20 and 80° C., and pressures between 1500 and 2500 psig.

The reaction chemistry is shown in FIG. 1, using various typical hexene isomers and glycerol as model reactants. These reactions can be carried out using branched olefins with carbon numbers of $C_5$ to $C_{12}$, or even higher and other polyols. As can be seen in FIG. 1, all the branched olefins with double bonds adjacent to a branch form a neo structure. If the double bond is in the carbon chain, but away from the branch, most of the time an isoester is formed, but even in this case some neoesters are formed due to isomerization of the location of the double bond, and/or structural isomerization in this very strong acid environment. For PVC plasticizer applications, it is desirable to maximize the neoalkylester content since neoesters are chemically much more stable, particularly to hydrolysis. In one form, the neoalkylester content may be at least 45 wt %, or at least 55 wt %, or at least 65 wt %, or at least 70 wt %, or at least 75 wt %, or at least 85 wt %, or at least 95 wt %, or at least 99 wt %, or 100 wt % of the plasticizer composition. The need to maximize the neoester content leads to a requirement to use highly branched olefin feeds. This requirement for highly branched olefin feeds may be fulfilled since the olefin oligomers produced by the common strong acid oligomerization processes typically result in olefin products that have 90% or more branched isomers. Required $C_5$ to $C_{12}$ branched olefin feedstocks are readily available and are produced by common commercial oligomerization processes designed to run on both refinery and steam cracked light olefin feeds.

A variety of polyols may be used including, but not limited to, ethylene glycol, polyethylene glycol, glycerol, pentaerythritol, trimethylol propane, propylene glycol, and polypropylene glycol. Since the polarity of the plasticizer needs to be balanced to achieve compatibility with PVC, it may be necessary to use olefins of higher or lower carbon numbers to achieve the desired polarity with the various optional polyols. It is also possible to use mixed carbon number olefins to achieve the desired mix of polarity and branching in the plasticizer.

The applicability of the hexene based triglyceride neoester structures shown in FIG. 1 as potential PVC plasticizers may be screened by estimating their relative solubility in PVC using Small's group contribution method (Small, P. A., "Some Factors Affecting the Solubility of Polymers", J. Appl. Chem., 3, pp 76-80 (1953)) to calculate solubility parameters for each structure. These calculations are shown below.

Figure 2:
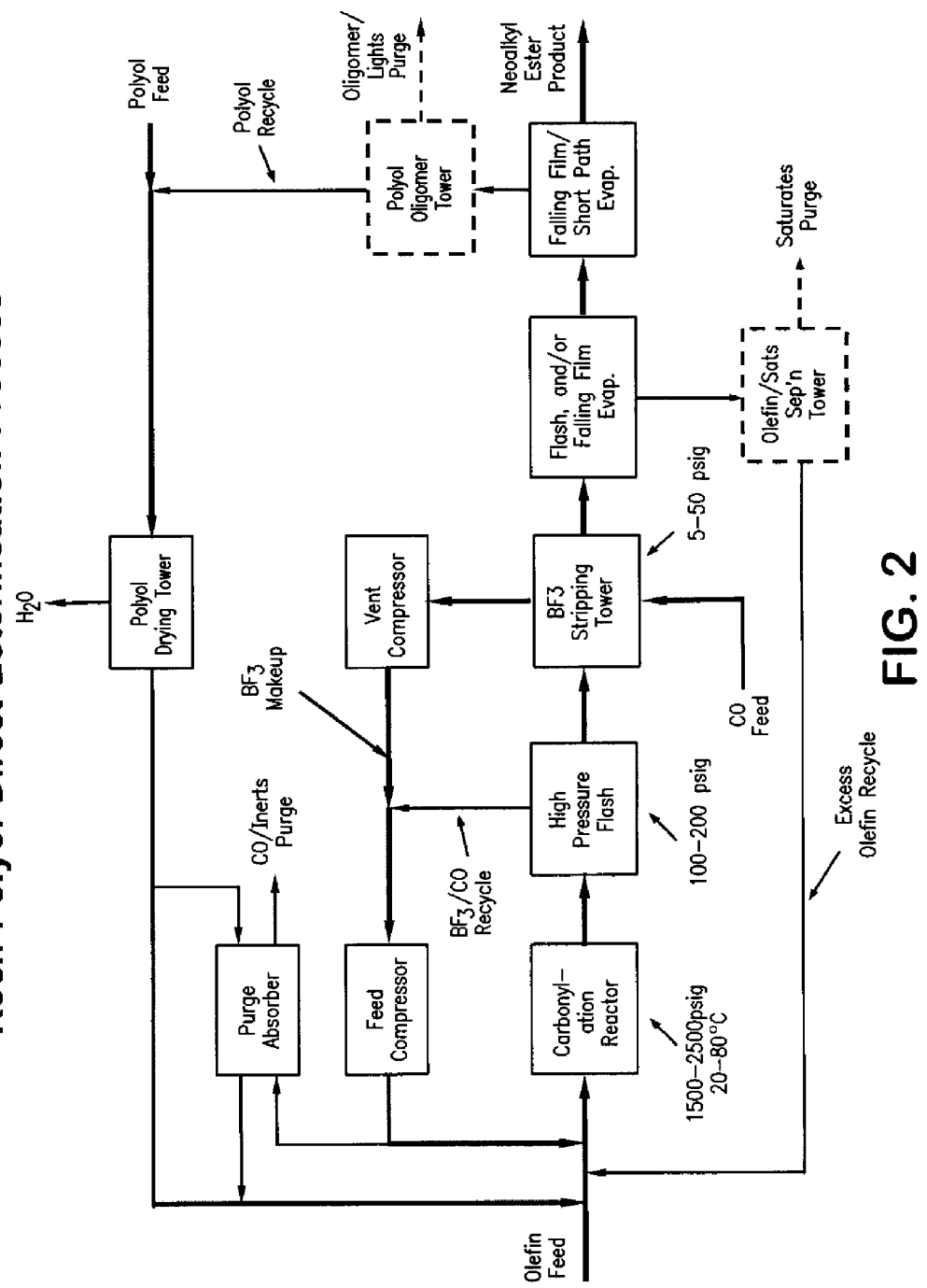
FIG. 2 is a process flow diagram of the Koch polyol direct esterification process of the present disclosure.

A simplified process diagram for carrying out the Koch chemistry described above is shown in FIG. 2. The polyol feedstream may be dried prior to feeding it to the reaction to avoid neoacids being produced rather than neoesters. In one non-limiting exemplary form, drying the polyol feedstream may be accomplished by first feeding the polyol feed to a distillation tower where the water is taken overhead as a volatile light component, and the water-free polyol is taken out the tower bottom. After drying, a small portion of the polyol feed is used to absorb $BF_3$ catalyst from a CO recycle inerts purge stream. Also, the feed carbon monoxide (CO) may be first used as a stripping medium to strip residual $BF_3$ from the reactor effluent before being compressed to reaction pressure. Then, olefin, polyol, and CO may be pumped or compressed up to reaction pressure at 1500 to 2500 psig, or 1700 to 2300 psig, or 1900 to 2100 psig, combined, and then introduced into the reactor having been cooled or heated to a reaction temperature of between 20 and 80° C., or between 30 and 70° C., or between 40 and 60° C. After exiting the reactor, the reaction mixture may be flashed in a high pressure flash at 100 to 200 psig, or 120 to 180 psig, or 140 to 160 psig to remove $BF_3$ and unreacted excess CO, which may be recycled back to the suction of the CO Feed Compressor. The flashed reactor effluent may then be heated and stripped of residual $BF_3$ in a $BF_3$ stripping tower using the fresh feed CO gas as the stripping medium. The CO gaseous effluent from the $BF_3$ stripper, containing a minor amount of $BF_3$, may then fed to the suction of a vent compressor to be then fed to the CO feed compressor for recycle back to the reactor. The reactor effluent, free of residual CO and $BF_3$, may then be heated and fed to a flash drum and/or a falling film evaporator to remove unreacted excess olefin for recycle back to the reactor. The process conditions in the flash and evaporator may be set at a temperature (for example, 20-250° C.) and pressure (for example, 1-760 mm Hg) to allow easy removal of the excess unreacted olefin. Following removal of residual olefin, the crude neoakylester product is fed to either a falling film or a short path evaporator for removal of any residual polyol, oligomers, or other light impurities.

Two additional exemplary non-limiting process steps may be utilized. One step is an olefin saturates separation tower for the excess olefin recycle stream for the case where there are excessive saturates in the olefin feed. A second step is a polyol-oligomer separation tower to remove olefin oligomers from the polyol recycle stream for the case where it is required.

In one form of the present disclosure, the polyol neoakylester plasticizer is "phthalate-free". As used in the instant specification and in the appended claims, the term "phthalate-free" means that the plasticizer does not contain any phthalate diesters, which are also known in the art simply as phthalates.

Referring to the polyol neoalkylester chemical formula below, for the instant application including the claims, the total carbon number of the neoalkyl ester groups is defined as the sum of the carbons for the $R^1$, $R^2$, $R^3$, $R^4$, $R^5$, $R^6$, $R^7$, $R^8$, and $R^9$ groups, plus the 3 carbons for the quaternary carbons bearing $R^1$-$R^9$, plus the 3 carbons for the three carbonyl groups, and not including the 3 glycerol backbone carbons. In one form of the instant application, the total carbon number of the neoalkylester groups range from 20 to 25. In another form of the instant application, the total carbon number of the neoalkylester groups range from 21 to 24. In yet another form, the total carbon number of the neoalkyl ester groups ranges from 22 to 23 carbons. For purposes of counting these carbons, the 'neoalkyl ester group' is considered to include the C=O group. For other purposes of defining the identities of groups $R^1$ through $R^9$ and defining the overall length of the alkyl substituent groups attached to the esters, the "neoalkyl group" is considered to comprise the $(-C(R^1)(R^2)(R^3)$, $-C(R^4)(R^5)(R^6)$, or $-C(R^7)(R^8)(R^9)$ group without the C=O group.

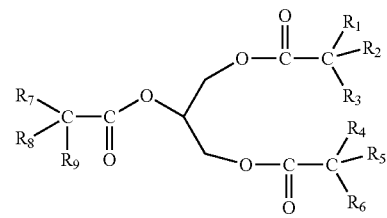

According to the present disclosure, the triglycerides disclosed herein may be produced by esterification of a neo acid (or a neo acid chloride) comprising one or more $C_5$ to $C_{13}$ neo acids to yield a triglyceride with a total carbon number of the neoalkyl triester groups ranging from 20 to 25 (including the three carbons for the quaternary carbons bearing $R^1$-$R^9$, the three carbons for the three carbonyl groups, and not including the three glycerol backbone carbons).

In some embodiments of the invention, the neo acids used to esterify the glycerol have an average branching of from about 2.0 to about 3.0 branches per molecule. In one embodiment, the average branching may range from about 2 to about 2.4 branches per molecule. In another embodiment, neo $C_5$ to $C_{13}$ acids are used having an average branching of from about 2.0 to about 3.0 branches per molecule, preferably from about 2.0 to about 2.5, more preferably from about 2.0 to about 2.2 branches per molecule. In yet other embodiments, the neo acids used may have the branching properties of their precursor olefins described in International Patent Applications WO03/082778 and WO03/082781, U.S. Patent Application US2005/0014630, or U.S. Pat. No. 7,507,868, all herein incorporated by reference. Nuclear Magnetic Resonance analyses of the branching found in the neo acids finds that these branches are typically methyl and ethyl groups.

The present disclosure is also directed to the product of the process, which comprises at least one compound according to the following structure (II):

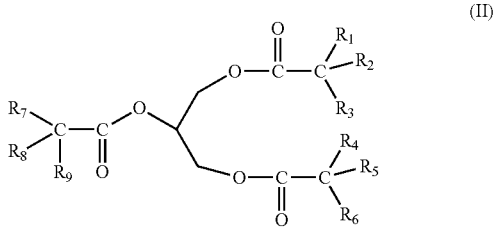

(II)

wherein the sum of the carbons for the neoalkyl ester groups ($R^1$, $R^2$, $R^3$, $R^4$, $R^5$, $R^6$, $R^7$, $R^8$, $R^9$, plus the three carbons for the quaternary carbons bearing $R^1$-$R^9$, plus the three carbons for the three carbonyl groups, and not including the three glyceryl backbone carbons) may range from 20 to 25, and wherein the product of the process comprises at least 45 wt % of the plasticizer composition. In other embodiments, the product of the above mentioned process comprises at least 55 wt %, or at least 65 wt %, or at least 70 wt %, or at least 75 wt %, or at least 85 wt %, or at least 95 wt %, or at least 99 wt %, or 100 wt % of the plasticizer composition. Alternatively, the sum of the carbons for the neoalkyl ester groups ($R^1$, $R^2$, $R^3$, $R^4$, $R^5$, $R^6$, $R^7$, $R^8$, $R^9$, plus the three carbons for the quaternary carbons bearing $R^1$-$R^9$, plus the three carbons for the three carbonyl groups, and not including the three glycerol backbone carbons) may range from 20 to 24, or 20 to 23, or 20 to 22, or 20 to 21, or 22 to 25, or 23 to 25, or 24 to 25. In another form, the sum of the carbons for the $R^1$, $R^2$, $R^3$, $R^4$, $R^5$, $R^6$, $R^7$, $R^8$, $R^9$, plus the three carbons for the quaternary carbons bearing $R^1$-$R^9$, plus the three carbons for the three carbonyl groups, and not including the 3 glycerol backbone carbons may be 20, or 21, or 22, or 23, or 24, or 25.

The present disclosure is also directed to the product of the process which comprises at least one compound according to structure (I), wherein the sum of the carbons for the neoalkyl ester groups ($R^1$, $R^2$, $R^3$, $R^4$, $R^5$, $R^6$, $R^7$, $R^8$, $R^9$, plus the three carbons for the quaternary carbons bearing $R^1$-$R^9$, plus the three carbons for the three carbonyl groups, and not including the three glycerol backbone carbons) may range from 20 to 25, and also wherein the neoalkyl groups (the —C(R1)(R2)(R3), —C(R4)(R5)(R6), and —C(R7)(R8)(R9) groups are independently selected from $C_4$ to $C_{12}$ alkyl groups having an average number of branches per group of from about 2.0 to about 3.0 branches per group. In one embodiment, the average branching may range from about 2.0 to about 2.4 branches per group. In another embodiment, the alkyl groups are $C_4$ to $C_{12}$ groups having an average branching of from about 2.0 to about 2.2 branches per group, preferably from about 2.0 to about 2.5, more preferably from about 2.0 to about 2.2 branches per group. In yet other embodiments, the alkyl groups used may have the branching properties of their precursor olefins described in International Patent Applications WO03/082778 and WO03/082781, U.S. Patent Application US2005/0014630, or U.S. Pat. No. 7,507,868, all herein incorporated by reference.

In yet another embodiment, the plasticizer composition may include 55 wt % or less of non-inventive triglycerides blended with inventive triglycerides. Non-limiting exemplary non-inventive triglycerides for blending include tribenzoate triglycerides, other triaryl triglycerides, neoalkyl triglycerides having a carbon number not between 20 and 25, branched alkyl triglycerides containing isomeric mixtures of non-neoalkyl groups or only some neoalkyl groups, mixed alkyl/benzyl triglycerides, and combinations thereof. In alternate embodiments, the non-inventive triglycerides described may constitute 45 wt % or less, 35 wt % or less, 25 wt % of less, 15 wt % or less, 10 wt % or less, 5 wt % or less, or 1 wt % or less of the total plasticizer composition.

In the first step of the process for producing the triglycerides disclosed herein, neo acids may be produced by carbonylation of $C_4$ to $C_{12}$ olefins that in turn have been produced by propylene, butene, and/or pentene oligomerization over solid phosphoric acid or zeolite catalysts. The oligomerization processes are per se well known. See, for instance, U.S. Pat. Nos. 7,253,330, and 7,145,049.

Optionally, an additional step in the process may include combining the $C_5$ to $C_{13}$ neo acid, or mixture of $C_5$ to $C_{13}$ neo acids, at a molar ratio of from 0.25:1 to 4:1 with benzoic acid, toluic acid or combinations thereof to form a mixed acid blend. When a blend of benzoic acid and toluic acid is used as the second component, the weight percent of benzoic acid may be from 10 wt % to 90 wt % with the remainder being toluic acid. For example, the benzoic acid may be 10, 20, 30, 40, 50, 60, 70, 80, or 90 wt % of the blend with the remainder being toluic acid. The molar ratio of $C_5$ to $C_{13}$ neo acid(s) to benzoic or toluic acid(s) in the mixed acid blend may be 1:1 or may range from 0.25:1 to 4:1, or 0.33:1 to 3:1, or 0.5:1 to 2:1, or 0.67:1 to 1.5:1. The toluic acid may include the ortho isomer, the meta isomer, the para isomer, and combinations thereof.

The next step in the process is the esterification of the $C_5$ to $C_{13}$ neo acid, or mixture of neo $C_5$ to $C_{13}$ acids (or, optionally, mixture of neo with benzoic and/or toluic acids) with glycerol to form a triglyceride. Alternatively, other polyols may be used to esterify the neo acid(s). Such polyols may have two alcohol groups, or three (as for glycerol), or four, or other quantity of multiple alcohol groups. Other non-limiting exemplary polyols include ethylene glycol, poly(ethylene glycol), pentaerythritol, trimethylol propane, propylene glycol, polypropylene glycol), triethylene glycol, triethylene glycol derivatives, as well as dimers of ethylene glycol and/or propylene glycol and other $C_2$ to $C_6$ diols or glycols. Mixtures of polyols may be used, such as a mixture of glycerol with propylene glycol, or a mixture of glycerol with triethylene glycol or a triethylene glycol derivative.

Glycerol is currently an attractive polyol for use to make plasticizers because it is abundantly available. It is, for instance, a major byproduct of biodiesel production. When glycerol is used, this process yields a neoalkyl triglyceride. The esterification step may be catalyzed by at least one metal selected from Ti, Zr or Sn, or a mixture thereof, or catalyzed by an organic acid.

In an alternative form, the esterification step may be uncatalyzed. Alternatively, the neo acid(s) may first be converted into the analogous acid chlorides and then reacted with the glycerol (or other polyol) to provide higher reactivity, if needed.

Crude glycerol may also be used. The term "crude glycerol" means a glycerol component including not more than 90 wt % of glycerol. Other components may include, but are not limited to, methanol, water, fatty acid, MONG (Matter Organic Not Glycerol), NaCl, ash and/or other impurities. In other forms, the crude glycerol may include not more than 95 wt %, or 90 wt %, or 88 wt %, or 86 wt %, or 84 wt %, or 82 wt %, or 50 wt % glycerol. The inorganic impurities are precipitated at the end of the esterification, and are removed by filtration and washing the ester with water. In other words, the esterification reaction is a means of purifying the crude glycerol. Non-limiting exemplary crude glycerols include REG, EIS-739, EIS-740, EIS-733, EIS-724, EIS 56-81-5, IRE and mixtures thereof.

In another form of the present disclosure, a mixture of crude glycerol with another polyol may be utilized to produce mixtures of triglycerides and other polyol esters that may be used as plasticizers. Other polyols that may be utilized with crude glycerol during the esterification process include, but are not limited to, ethylene glycol, poly(ethylene glycol), propylene glycol, polypropylene glycol), triethylene glycol and triethylene glycol derivatives, dimers of ethylene glycol and/or propylene glycol, and other $C_2$ to $C_6$ diols or glycols. Mixtures of crude glycerol with these polyols, such as ethylene glycol, propylene glycol, and/or triethylene glycol, may include at least 20 wt %, or least 40 wt %, or least 60 wt %, or least 80 wt % crude glycerol, with the remainder constituting the other polyol. It is preferred that the polyols as part of the crude glycerol or mixtures of crude glycerol with other polyols be fully esterified so that there are a low to negligible amount of free hydroxyl groups. Thus, for example, it is preferred that the glycerol component of the crude glycerol is esterified to the triester.

Single carbon number neo acids (or acid chlorides) can be used in the esterification, or neo acids of differing carbon numbers can be used to optimize product cost and performance requirements. Hence, the neo acids may be esterifed to form mixed triglycerides bearing neoalkyl sidechains of different carbon numbers, wherein the total number of carbons for the neoalkyl ester groups ($R^1$, $R^2$, $R^3$, $R^4$, $R^5$, $R^6$, $R^7$, $R^8$, $R^9$, plus the three carbons for the quarternary carbons bearing $R^1$-$R^9$, plus the three carbons for the three carbonyl groups, and not including the three glycerol backbone carbons) may range from 20 to 25. Such range of total carbons for the triester groups yields neo triglycerides with good performance when used as plasticizers for polymeric resins. More particularly, such triglycerides have been discovered to give good compatibility and low volatility with a broad range of polymeric resins, including PVC. Such triglycerides also yield good low temperature performance properties, and, critically, enhanced hydrolytic stability as compared to non-tri-neoalkyl triglycerides.

In cases where a mixture of neo acids of varying carbon numbers is used to prepare the triglyceride ester, the product will consist of a mixture of triglycerides having different chain lengths (for example, acids of carbon number A and B would generate triglycerides having chains of length AAA, ABA/AAB, BAB/BBA, and BBB). For optimal performance it may be desirable to remove certain triglyceride components with high or low carbon numbers from the mixture, or to enrich the mixture with triglycerides of certain carbon number. Thus, the optional next step in the process is purifying the neoalkyltriglyceride to form a plasticizer, wherein the total carbon number of the neoalkyl ester groups ($R^1$, $R^2$, $R^3$, $R^4$, $R^5$, $R^6$, $R^7$, $R^8$, $R^9$, plus the three carbons for the quaternary carbons bearing $R^1$-$R^9$, plus the three carbons for the three carbonyl groups, and not including the three glycerol backbone carbons), ranges from 20 to 25 for greater than or equal to 45 wt % of the plasticizer.

Following the esterification process, a fractionation process, such as distillation, may be used to separate the $C_{20}$ to $C_{25}$ triglycerides from the lighter and heavier triglycerides. The light triglycerides may be recycled back to the esterification step of the process, to undergo transesterification into the desired $C_{20}$ to $C_{25}$ triglycerides. The heavy triglycerides may also be recycled back to the esterification step of the process after adding fresh acids and glycerol. Note, however that these $C_{20}$ to $C_{25}$ triglycerides may include other proportions (55 wt % or less relative to the total) of triglycerides which do not have a total carbon number of the triester groups falling within the 20 to 25 range. If the total weight % of these non-inventive, non-$C_{20}$ to $C_{25}$ triglycerides is greater than 55 wt %, plasticizer properties (volatility, compatibility, low temperature performance, etc.) will begin to be negatively impacted. Hence, for the $C_{20}$ to $C_{25}$ triglycerides disclosed herein, neoalkyl triglycerides with a total carbon number of from 20 to 25 should comprise greater than or equal to 45 wt %, or greater than or equal to 50 wt %, or greater than or equal to 55 wt %, or greater than or equal to 60 wt %, or greater than or equal to 65 wt %, or greater than or equal to 70 wt %, or greater than or equal to 75 wt %, or greater than or equal to 90 wt %, or greater than or equal to 95 wt %, or greater than or equal to 97 wt %, or greater than or equal to 99 wt %, or greater than or equal to 99.5 wt %, or greater than or equal to 99.9 wt % of the plasticizer. The fractionation process following the esterification step may be used to increase the purity of $C_{20}$ to $C_{25}$ triglycerides.

The applicability of the neoalkyl triglyceride structures as potential PVC plasticizers can be screened by estimating their relative solubility in PVC using Small's group contribution method to calculate solubility parameters for each structure (see: (a) The Technology of Plasticizers by J. Sears and J. Darbey, John Wiley & Sons, New York, 1982, pp 95-99, discussing use of Small's formula to predict plasticizer compatibility with PVC; (b) Small, P. A., "Some Factors Affecting the Solubility of Polymers", J. Appl. Chem, 3, pp 76-80 (1953) which cites Small's original work as a reference; (c) Polymer Handbook, 3rd Ed., J. Brandrup & E. H. Immergut, Eds. John Wiley, New York, (1989), which includes use of Small's group contribution values). It is noted that solubility parameter data alone does not predict other critical performance factors, such as volatility, in addition to compatibility with PVC. These calculations are shown below in Table 1 for diisononyl phthalate (DINP) as a reference (MW=molecular weight):

TABLE 1

| DINP | Polarity | Number of Groups | Solubility Contribution | MW | MW Contribution |
|---|---|---|---|---|---|
| $CH_3$ | 214 | 2 | 428 | 15 | 30 |
| —$CH_2$— | 133 | 16 | 2128 | 14 | 224 |
| COO esters | 310 | 2 | 620 | 44 | 88 |
| Phenylene | 658 | 1 | 658 | 76 | 76 |
| | | | 3834 | | 418 |
| | | Solubility Parameter = | 8.878737 | Density = | 0.968 |
| | | Delta to PVC = | −0.78126 | | |

Table 2 presents solubility parameter calculations for the three isomers of neo $C_7$ triglyceride (see Example 2 for further descriptions of the isomers).

TABLE 2

Small's Solubility Parameters for
C7 Branched Neoester Triglycerides

| | Solubility | Number | Solubility Contrib | MW | MW Contrib |
|---|---|---|---|---|---|
| Dimethyl neopentanoic acid triglyceride | | | | | |
| CH3 | 214 | 9 | 1926 | 15 | 135 |
| —CH2— | 133 | 8 | 1064 | 14 | 112 |
| —CH= | 28 | 1 | 28 | 13 | 13 |
| =C= | 93 | 3 | 279 | 12 | 36 |
| COO esters | 310 | 3 | 930 | 44 | 132 |
| | | | 4227 | | 428 |
| Solubility Parameter = | | | 9.48 | Density = | 0.96 |
| Delta to PVC = | | | −0.18 | | |
| Ethyl methyl neobutanoic acid triglyceride | | | | | |
| CH3 | 214 | 9 | 1926 | 15 | 135 |
| —CH2— | 133 | 8 | 1064 | 14 | 112 |
| —CH= | 28 | 1 | 28 | 13 | 13 |
| =C= | 93 | 3 | 279 | 12 | 36 |
| COO esters | 310 | 3 | 930 | 44 | 132 |
| | | | 4227 | | 428 |
| Solubility Parameter = | | | 9.48 | Density = | 0.96 |
| Delta to PVC = | | | −0.18 | | |
| Trimethyl neobutanoic acid triglyceride | | | | | |
| CH3 | 214 | 12 | 2568 | 15 | 180 |
| —CH2— | 133 | 2 | 266 | 14 | 28 |
| —CH= | 28 | 4 | 112 | 13 | 52 |
| =C= | 93 | 3 | 279 | 12 | 36 |
| COO esters | 310 | 3 | 930 | 44 | 132 |
| | | | 4155 | | 428 |
| Solubility Parameter = | | | 9.32 | Density = | 0.96 |
| Delta to PVC = | | | −0.34 | | |

The solubility parameter of PVC is calculated by the same method to be 9.66. The differences in solubility parameters between the triglyceride structures in FIG. 1 and PVC are shown in Table 2. These differences from PVC range from 0.18 to 0.34 units, which indicate good expected solubility in PVC. As references, the Small's solubility parameters for two well know phthalate plasticizers, DINP and DIDP (diisodecyl phthalate) are 8.88 (delta to PVC=0.78, as shown in Table 1) and 8.56 (delta to PVC=1.10), respectively. The estimated solubility parameter for one non-phthalate plasticizer, DINCH (di-isononyl cyclohexanoate), is 7.32 by Small's method. This is a difference of 2.34 solubility parameter units from PVC, yet DINCH is still used as a PVC plasticizer. Thus, based on their estimated solubility in PVC based on Small's method, the heptanoic neoester triglyceride structures shown in FIG. 1 can be expected to have utility as plasticizers for PVC as their estimated solubility parameters are in ranges similar to that of commercial plasticizers.

The plasticizers according to the current disclosure may also be used with polyvinyl chlorides, polyesters, polyurethanes, ethylene-vinyl acetate copolymer, rubbers, acrylics, and polymer blends, such as blends of polyvinyl chloride with an ethylene-vinyl acetate copolymer or polyvinyl chloride with a polyurethane or ethylene-type polymer.

In particular, the neoalkyl triglyceride plasticizers disclosed herein yield improved hydrolytic stability and resistance in resin compositions as compared to trialkyl triglycerides with non-neo structures. Stability to ester group hydrolysis is an important parameter for plasticizer performance. Hydrolysis to free acids and mono- and diglycerides may cause decreased compatibility and increased volatility, which in turn affect many other aspects of plasticization behavior over time. Hydrolytic stability is measured via acid and glycerol formation stability in the resin composition. This may be quantified by measuring the hydrolysis products by gas chromatography of resin compositions including the inventive plasticizers disclosed herein. The hydrolysis products of the resin compositions including the plasticizers disclosed herein may be less than 5 wt %, or less than 2 wt %, or less than 1 wt %, or less than 0.5 wt %, or less than 0.4 wt %, or less than 0.3 wt %, or less than 0.2 wt %, or less than 0.1 wt % of the mixture of the resin and plasticizer following melt processing as measured by gas chromatography.

EXAMPLES

Example 1

Synthesis of Neo $C_7$ Triglyceride

Glycerol (39.77 g, 0.432 mole) and neoheptanoic acid (225.2 g, 1.73 mole) (see details for this material in Example 2) were charged into a 4-necked, 500 mL round bottom flask equipped with an air stirrer, thermometer, nitrogen inductor, Dean-Stark trap and a reflux condenser. The reaction mixture was heated for 16 hours at 192-225° C. 91% conversion (by water removal) was observed after 7 hours. The excess acid was removed by distillation under vacuum to 0.2 mm Hg. The crude product was then washed with a 10% aqueous sodium carbonate solution, followed by a distilled water wash. The organic layer was then dried over magnesium sulfate with stirring for 2 hours at room temperature. The crude residual product was 98% pure by gas chromatography and was combined with a second batch indicated in the next paragraph. Gas chromatography analysis was conducted using a Hewlett-Packard 5890 GC equipped with a HP6890 autosampler, a HP flame-ionization detector, and a J&W Scientific DB-1 30 meter column (0.32 micrometer inner diameter, 1 micron film thickness, 100% dimethylpolysiloxane coating). The initial oven temperature was 60° C.; injector temperature 290° C.; detector temperature 300° C.; the temperature ramp rate from 60 to 300° C. was 10° C./minute with a hold at 300° C. for 14 minutes. The calculated %'s reported for products were obtained from peak area, with an FID detector uncorrected for response factors.

The Neo $C_7$ triglyceride synthesis was repeated. Glycerol (115.1 g, 1.25 mole) and neoheptanoic acid (976.5 g, 7.5 mole) were added to a 4-necked 2 L round bottom flask and 30.1 g neoheptanoic acid was added to the Dean-Stark trap. In this case the acid-to-glycerol ratio was 6 to 1 rather than 4 to 1. The reaction mixture was heated 13 hours at 200-216° C. 100% conversion was observed after 8 hours heating by water removal. The reaction products from both experiments were combined and the excess acids were removed by distillation using a 3 foot Oldershaw column under vacuum to 0.10 mm The crude residual product was treated with decolorizing charcoal (1 wt %) by stirring at room temperature for 2 hours. The treated product was filtered twice to remove the charcoal. The clear and colorless liquid triglyceride product was 99.94% pure.

Example 2

Synthesis of Neo $C_7$ Triglyceride by Acid Chloride Route

A 604.45 g (2.3 mol, 1 eq.) portion of $PPh_3$ was dissolved in 724 mL $CCl_4$ in a 2 L three-necked round-bottom flask under N$_2$ to give a hazy solution. A stirbar was added and the flask was fitted with a water-cooled condenser topped with a N$_2$ inlet/outlet, mechanical stirrer and shaft, and an addition funnel. The addition funnel was charged with a solution of ExxonMobil Neoheptanoic Acid Prime (300 g, 2.30 mol uncorrected for purity) in 300 mL CCl$_4$. This material was 94.1% purity with an isomer balance of 43.0% 2,2-dimethylpentanoic acid (DMPA), 37.6% 2-ethyl-2-methylbutanoic acid (EMBA), and 13.5% 2,2,3-trimethylbutanoic acid (TMBA) by GC analysis (using FID detection; uncorrected for response factor). The acid solution was added dropwise at room temperature while stirring over a 1 hour period. No immediate reaction was observed other than a decrease in haziness to give a clear solution. After stirring under N$_2$ for an additional hour at room temperature, the addition funnel was removed and the contents of the flask were heated at reflux (~80° C.) for 3 h. The formation of a white precipitate was observed upon heating. Subsequently, the mixture was cooled to room temperature and filtered. Solvent was removed from the filtrate using a rotary evaporator. The residue was cooled in a refrigerator for 24 h and subsequently crushed with a spatula and extracted with 800 mL hexane for 2 hours. Solids were removed by filtration and the hexane filtrate depleted of volatiles using a rotary evaporator and high vacuum (at 50° C.) to give 200 g of a crude material containing product, phosphine-containing residues, unreacted acid, and other species (most likely neoheptanoic anhydrides). Fractional distillation of the crude material gave neoheptanoic acid chloride as the first boiling fraction (50° C./2.4×10$^{-2}$ torr; 57.4 g, 17%); higher boiling fractions contained species assigned as neoheptanoic anhydrides ($^{13}$C NMR C=O 173.1-173.0 ppm; IR $\upsilon_{C=O}$ 1808 and 1741 cm$^{-1}$) and free acids. Elemental analysis calc. for C$_{17}$H$_{13}$ClO: C, 56.57; H, 8.82; Cl, 23.85; O, 10.76. Found: C, 56.64; H, 8.96; Cl, 23.60. $^1$H NMR (CDCl$_3$, 400 MHz): δ 2.17 (septet, J=6.9 Hz, CHMe$_2$ of TMBA), 1.81 (app. sextet, J=7.3 Hz), 1.64-1.53 (m), and 1.35-1.29 (m) (probably CH$_2$ groups of EMBA and DMPA), 1.28 (s, probably CMe$_2$ of DMPA), 1.21 and 1.20 (2 singlets, probably C MeEt of EMBA and CMe$_2$ of TMBA), 0.94-0.88 (m, CHMe$_2$ of TMBA, CH$_2$Me of EMBA, and CH$_2$Me of DMPA). $^{13}$C NMR (CDCl$_3$, 125 MHz): δ 180.53 (C=O of TMBA), 180.11 (C=O of DMPA), 179.75 (C=O of EMBA), 57.23 (CMeEt of EMBA), 56.17 (CMe$_2$ of TMBA), 52.84 (CMe$_2$ of DMPA), 42.55 (CH$_2$ of DMPA), 34.34 (CHMe$_2$ of TMBA), 31.41 (CH$_2$ of EMBA), 25.11 (CMe$_2$ of DMPA), 21.46 (CMe$_2$ of TMBA), 20.38 (CMeEt of EMBA), 17.93 (CH$_2$Me of DMPA), 17.22 (CHMe$_2$ of TMBA), 14.32 (CH$_2$Me of DMPA), 8.58 (CH$_2$Me of EMBA). Isomer ratio (average of C=O and CR$_2$ resonances): 12.6% TMBA, 42.1% EMBA, 45.4% DMPA. IR (NaCl disk): 2970 (s), 2940 (sh), 2877 (sh), 1789 (vs, $\upsilon_{C=O}$), 1698 (m, may be acid $\upsilon_{C=O}$ from incidental hydrolysis), 1460 (m), 1387 (w), 1369 (sh), 1194 (w), 1066 (w), 1009 (w), 975 (w), 961 (w), 916 (vs), 888 (m), 864 (m), 804 (vs), 756 (w), 743 (w) cm$^1$.

Subsequently, a 250 mL three-necked round bottomed flask was fitted with a condenser, magnetic stirbar, addition funnel, and nitrogen purge inlet. Glycerol (6.4 g, 69.5 mmol, dried over 5 Å molecular sieves), pyridine (19.2 g, 243 mmol), and 50 mL anhydrous ethyl ether were added to the flask, and its contents (slightly cloudy solution) were heated to gentle ether reflux. The addition funnel was charged with neoheptanoic acid chloride (30 g, 230 mmol) which was added to the glycerol solution dropwise over a ½ hour period. Formation of a Ph$_3$P=O precipitate was observed. Subsequently, the contents of the flask were maintained at reflux for 1 h, then cooled, and liquids were separated from the precipitate by filtration. The filtrate was concentrated using a rotary evaporator, causing precipitation of additional solids, and cooled in a refrigerator overnight. These solids were separated from liquid supernatant, stirred with hexanes, and filtered; hexanes were removed from the filtrate wand the residue combined with the liquids from the first filtration step. The combined crude material was fractionally distilled at 3×10$^{-3}$ mm Hg; a first cut (7.75 g) distilling at 65° C. contained only lights by GC analysis (monoglycerides and byproducts); a second cut (11.3 g) distilling at 160-165° C. contained the triglyceride along with other less substituted species. This distillate was then fractionally redistilled at 1 mm Hg/220° C. A first cut (6.2 g) contained significant amounts of both di- and triglyceride; a second cut (2.35 g) contained 92.1% triglyceride (with 5.8% diglyceride) and was not further purified.

Example 3

Synthesis of Neo C$_9$ Triglyceride

Glycerol (41.8 g, 0.454 mole), neononanoic acids (431.6 g, 2.722 mole; isomer mixture distilled from ExxonMobil Neo 9-13 Carboxylic Acids) and m-xylene (30.0 g, 0.283 mole) were charged into a 4-necked-1000 mL round bottom flask equipped with an air stirrer, thermometer, nitrogen inductor, Dean-Stark trap and a reflux condenser. The reaction mixture was heated for 17 hours at 212-220° C. The excess acid was removed by distillation under vacuum to 0.1 mm. The crude residual product was 100% pure by GC and was not distilled.

Example 4

Synthesis of Mixed Pivalic/Neo C$_9$ Triglyceride

Glycerol (144 g, 1.561 mole), neononanoic acids (474.0 g, 2.98 mole, as in Example 2), pivalic acid (2,2-dimethylpropionic acid, 318.8 g, 3.122 mole) and mixed xylenes (470.0 g, 4.43 mole) were charged into a 4-necked, 2000 mL round bottom flask equipped with an air stirrer, thermometer, nitrogen inductor, Dean-Stark trap and a reflux condenser. The reaction mixture was heated for 25 hours at 153-220° C. The reaction was slow at the lower temperatures so xylenes were removed and the reaction mixture temperature was allowed to climb to obtain higher conversion. After heating 24 hours, the conversion based on water removal was 91%. The reaction mixture was fractionated using a Claisen adapter. The following fractions and retains were obtained (555 TG=triglyceride with three pivalic (C$_5$) sidechains; 999 TG=triglyceride with three neononanoic (C$_9$) chains, etc.; as by GC):

Material 4a: concentrated mixture prior to distillation; 99.70% triglyceride esters containing 4.3% 555 TG, 32.5% 559 TG, 53.6% 599 TG, and 9.2% 999 TG.

Material 4b: distillate cut; 99.42% triglyceride esters containing 15% 555 TG, 57% 559 TG, 27% 599 TG, and 0.42% 999 TG.

Material 4c: distillate cut; 99.74% triglyceride esters containing 0.44% 555 TG, 8.6% 559 TG, 75.2% 599 TG, and 15.5% 999 TG.

Example 5

Differential Scanning Calorimetry (DSC), Viscosity, and Thermogravimetric Analysis (TGA) Property Study of Neat Plasticizers Thermogravimetric Analysis (TGA) was conducted on the neat plasticizers using a TA Instruments AutoTGA 2950HR instrument (25-600° C., 10° C./min, under 60 cc N₂/min flow through furnace and 40 cc N₂/min flow through balance; sample size 10-20 mg). Table 3 provides a volatility comparison. Differential Scanning Calorimetry (DSC) was also performed on the neat plasticizers, using a TA Instruments 2920 calorimeter fitted with a liquid N₂ cooling accessory. Samples were loaded at room temperature and cooled to about −130° C. at 10° C./min and analyzed on heating to 75° C. at a rate of 10° C./min. Table 3 provides a glass transition ($T_g$) comparison. $T_g$s given in Table 3 are midpoints of the second heats (unless only one heat cycle was performed, in which case the first heat $T_g$, which is typically in very close agreement, is given). Kinematic Viscosity (KV) was measured at 20° C. according to ASTM D-445-20, the disclosure of which is incorporated herein by reference. Comparative data for DINP is also included.

TABLE 2

Volatility, Viscosity, and Glass Transition Properties of Neat Plasticizers.

| Ex. No. | TGA 1% Wt Loss (° C.) | TGA 5% Wt Loss (° C.) | TGA 10% Wt Loss (° C.) | TGA Wt Loss at 220° C. (%) | DSC $T_g$ (° C.) | KV (20° C., mm²/sec) |
|---|---|---|---|---|---|---|
| DINP | 184.6 | 215.2 | 228.5 | 6.4 | −79.1 | 96.81 |
| 1 | 151.1 | 179.0 | 192.8 | 32.6 | −82.8 | 329 |
| 3 | 172.6 | 204.2 | 219.3 | 10.2 | −53.8 | 2789.89 |
| 4a | 134.7 | 165.1 | 180.1 | 44.5 | −56.4 | — |
| 4b | 119.4 | 151.3 | 166.7 | 32.2 | −59.1 | — |
| 4c | 141.7 | 170.0 | 184.5 | 41.4 | −56.8 | — |

— Data not taken.

Example 6

Figure 3:
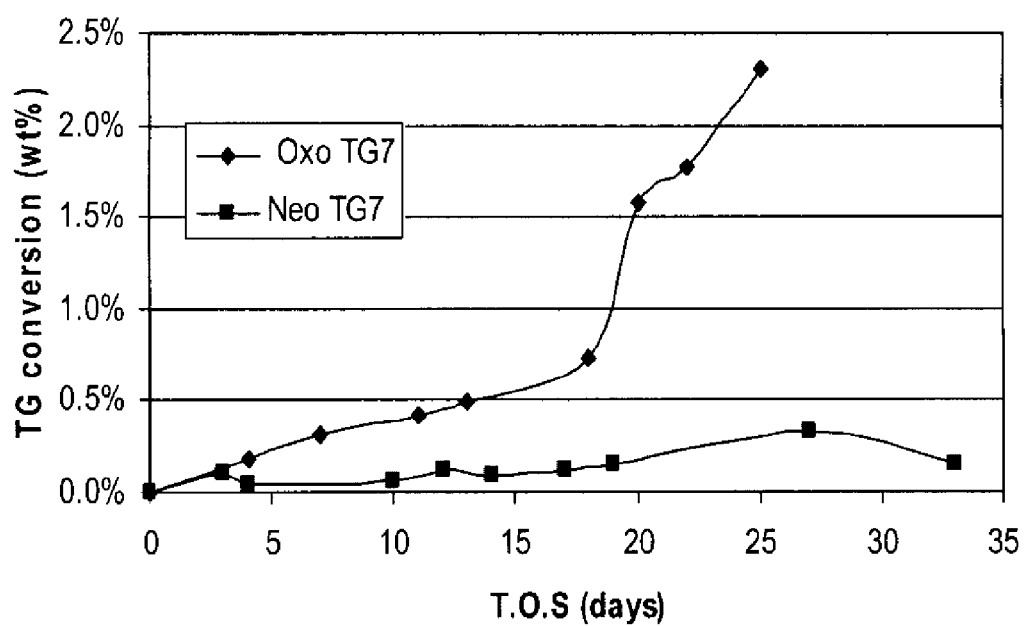
FIG. 3 shows hydrolytic stability test results as measured by triglyceride conversion into hydrolysis products versus time on stream for Oxo $C_7$ triglyceride and Neo $C_7$ triglyceride as described in Example 6.

Hydrolytic Stability Comparison Between Neo C₇ Triglyceride and Oxo C₇ Triglyceride A 120 mL glass Parr reactor was charged with 25 grams of a 0.05N HCl solution plus 75 grams of either the Neo C₇ triglyceride ester prepared in Example 1, or a C₇ triglyceride having three sidechains derived from ExxonMobil Oxo C₇ acids. The latter material ("Oxo C₇ triglyceride") was 100% triglyceride by GC and was prepared from an Oxo C₇ acid mixture that contained several differently branched isomers but no neo acid structures. The mixture was stirred for 33 days at 91-104° C. with GC sampling throughout the heating period to quantify the amount of triglyceride hydrolyzed to diglyceride or other byproducts ("% TG conversion"). Data are shown in FIG. 3. The neo triglyceride shows much greater hydrolytic stability as compared to the Oxo triglyceride.

Example 7

General Procedure for Plasticization of Poly(vinyl chloride) with Neo Triglyceride Esters A 5.85 g portion of the desired neo triglyceride ester (or comparative commercial plasticizer DINP) was weighed into an Erlenmeyer flask which had previously been rinsed with uninhibited tetrahydrofuran (THF) to remove dust. An 0.82 g portion of a 70:30 by weight solid mixture of powdered Drapex® 6.8 (Crompton Corp.) and Mark® 4716 (Chemtura USA Corp.) stabilizers was added along with a stirbar. The solids were dissolved in 117 mL uninhibited THF. Oxy Vinyls® 240F PVC (11.7 g) was added in powdered form and the contents of the flask were stirred overnight at room temperature until dissolution of the PVC was complete (a PVC solution for preparation of an unplasticized comparative sample was prepared using an identical amount of stabilizer, 100 mL solvent, and 13.5 g PVC). The clear solution was poured evenly into a flat aluminum paint can lid (previously rinsed with inhibitor-free THF to remove dust) of dimensions 7.5" diameter and 0.5" depth. The lid was placed into an oven at 60° C. for 2 hours with a moderate nitrogen purge. The pan was removed from the oven and allowed to cool for a ~5 min period. The resultant clear film was carefully peeled off of the aluminum, flipped over, and placed back evenly into the pan. The pan was then placed in a vacuum oven at 70° C. overnight to remove residual THF. The dry, flexible, typically almost colorless film was carefully peeled away and exhibited no oiliness or inhomogeneity unless otherwise noted. The film was cut into small pieces to be used for preparation of test bars by compression molding (size of pieces was similar to the hole dimensions of the mold plate). The film pieces were stacked into the holes of a multi-hole steel mold plate, preheated to 170° C., having hole dimensions 20 mm×12.8 mm×1.8 mm (ASTM D1693-95 dimensions). The mold plate was pressed in a PHI company QL-433-6-M2 model hydraulic press equipped with separate heating and cooling platforms. The upper and lower press plates were covered in Teflon™-coated aluminum foil and the following multistage press procedure was used at 170° C. with no release between stages: (1) 3 minutes with 1-2 tons overpressure; (2) 1 minute at 10 tons; (3) 1 minute at 15 tons; (4) 3 minutes at 30 tons; (5) release and 3 minutes in the cooling stage of the press (7° C.) at 30 tons. A knockout tool was then used to remove the sample bars with minimal flexion. Typically near-colorless, flexible bars were obtained which, when stored at room temperature, showed no oiliness or exudation several weeks after pressing unless otherwise noted.

Example 8

Properties of PVC Bars Plasticized with Neo Triglyceride Esters

Two each of the sample bars prepared in Example 7 were visually evaluated for appearance and clarity and further compared to identically prepared bars plasticized with DINP by placing the bars over a standard printed text. The qualitative and relative flexibility of the bars was also crudely evaluated by hand. The various bars were evaluated in different test batches; thus, a new DINP control bar was included with each batch. The bars were placed in aluminum pans which were then placed inside a glass crystallization dish covered with a watch glass. The bars were allowed to sit under ambient conditions at room temperature for at least three weeks and re-evaluated during and/or at the end of this aging period. Table 4 presents appearance rankings and notes. The comments in Table 4 demonstrate the following: (1) triglycerides with three neo $C_7$ chains are compatible with PVC as plasticizers; (2) triglycerides with three neo $C_9$ chains are incompatible and poor plasticizers: (3) replacing some neo $C_9$ chains with neo $C_5$ chains in the neo $C_9$ triglyceride gives materials that are compatible as plasticizers, if the product mixture contains low amounts of species with two neo $C_9$ chains.

time intervals were recorded and results were averaged between the bars. The averaged results are shown in Table 5. Notes on the appearance and flexibility of the bars at the end of the test are also given. The final color of the bars (even DINP control samples) varied between batches; gross comparisons only should be made between bars of different test batches.

TABLE 5

% Weight Loss at 98° C. of Plasticized PVC Bars.

| Example No. (Used in Bar) | Day 1 | Day 2 | Day 3 | Day 7 | Day 14 | Day 21 | Notes on Bar[a] |
|---|---|---|---|---|---|---|---|
| 1 | — | — | — | — | — | — | — |
| 1 (repeat) | 0.77 | 1.24 | 1.68 | 3.35 | 5.43 | 6.68 | Dark brown, buckled, brittle |
| 3 | 0.73 | 0.88 | 0.99 | 1.20 | 1.60 | 1.96 | Dark brown, opaque, oily, brittle |
| 4a | 1.02 | — | 2.17[b] | 2.26 | 3.36 | 3.53 | Lt orange, curled, completely brittle |
| 4b | 0.95 | — | 1.67[b] | 2.39 | 3.93 | 4.70 | Lt orange, curled, completely brittle |
| 4c | 0.95 | — | 1.78[b] | 1.83 | 3.17 | 3.31 | Lt orange, curled, oily |
| DINP ctrl, ex. 1 | 0.27 | 0.32 | 0.42 | 0.32 | 0.72 | 1.10 | Yellow spots, still flexible |
| DINP ctrl, ex. 3 | 0.26 | 0.33 | 0.40 | 0.55 | 0.73 | 0.83 | Med brown, slight loss of flex |
| DINP ctrl, ex. 4 | 0.24 | — | 0.22[b] | 0.38 | 0.55 | 0.75 | Lt orange, good flex |

— Data not taken. Bars did not exhibit oiliness, stickiness, or inhomogeneity unless noted.
[a]See notes in Table 3 regarding initial color of neat plasticizers and bars.
[b]Day 5.

TABLE 4

Initial and Room Temperature Aging Clarity and Appearance Properties of Plasticized PVC Bars.

| Example No. (Plasticizer Used in Bar) | Initial Clarity Value* | Final Clarity Value (day of evaluation) | Notes on Bar at End of Test |
|---|---|---|---|
| 1 | —[a] | — | — |
| 1 (repeat) | 1 | 1 (21) | — |
| 3 | 3.5[b] | 3.5 (29) | Inhomog. Day 0; oily Day 3; brittle |
| 4a | 1[c] | 1 (23) | Very stiff, minor oiliness by Day 19 |
| 4b | 1[c] | 1 (23) | Very stiff |
| 4c | 1[c] | 1 (23) | Very stiff, minor oiliness by Day 13 |
| DINP ctrl for ex. 1 | 1 | 1 (21) | — |
| DINP ctrl for ex. 3 | 1[b] | 1 (29) | Light color |
| DINP ctrl for ex. 4 | 1[c] | 1 (23) | Somewhat stiff |

*1-5 scale, 1 = no distortion, 5 = completely opaque. — Data not taken. No bars exhibited oiliness, stickiness, or inhomogeneity unless noted. Bars reflected color, if any, of neat plasticizers.
[a]Film precursor to bar showed an oil spot; bar showed no oiliness or inhomogeneity.
[b]Evaluated 3 days after pressing.
[c]Evaluated 13 days after pressing.

Example 9

98° C. Weight Loss Study of Plasticized PVC Bars

Two each of the PVC sample bars prepared in Example 7 were placed separately in aluminum weighing pans and placed inside a convection oven at 98° C. Initial weight measurements of the hot bars and measurements taken at specified Example 10

Thermogravimetric Analysis (TGA) Property Study of Plasticized PVC Bars

The sample bars prepared in Example 7 were subjected to Thermogravimetric Analysis as described in Example 5 to evaluate plasticizer volatility in the formulated test bars. Table 6 provides a volatility comparison.

TABLE 6

Volatility Properties of Plasticizers in Plasticized PVC Bars.

| Example No. (Plasticizer Used in Bar) | TGA 1% Wt Loss (° C.) | TGA 5% Wt Loss (° C.) | TGA 10% Wt Loss (° C.) | TGA Wt Loss at 220° C. (%) |
|---|---|---|---|---|
| None (neat PVC)[a] | 129.9 | 192.3 | 255.4 | 6.3 |
| 1 | 165.1 | 202.3 | 234.9 | 7.8 |
| 1 (repeat) | — | — | — | — |
| 3 | — | — | — | — |
| 4a | — | — | — | — |
| 4b | — | — | — | — |
| 4c | — | — | — | — |
| DINP | 204.6 | 247.4 | 257.6 | 1.8 |

— Data not taken.

Example 11

70° C. Humid Aging Study of Plasticized PVC Bars

Using a standard one-hole office paper hole punch, holes were punched in two each of the sample bars prepared in Example 7 about ⅛" from one end of the bar. The bars were hung in a glass pint jar (2 bars per jar) fitted with a copper insert providing a stand and hook. The jar was filled with ~½" of distilled water and the copper insert was adjusted so that the bottom of each bar was ~1" above the water level. The jar was sealed, placed in a 70° C. convection oven, and further sealed by winding Teflon™ tape around the edge of the lid. After 21 days the jars were removed from the oven, allowed to cool for ~20 minutes, opened, and the removed bars were allowed to sit under ambient conditions in aluminum pans (with the bars propped at an angle to allow air flow on both faces) or hanging from the copper inserts for ca. 1 week (until reversible humidity-induced opacity had disappeared). The bars were evaluated visually for clarity. All bars exhibited complete opacity during the duration of the test and for several days after removal from the oven. Results are shown in Table 7. Notes on the appearance and flexibility of the bars at the end of the test are also given.

TABLE 7

70° C. Humid Aging Clarity and Appearance Properties of Plasticized PVC Bars.

| Example No. (Plasticizer Used in Bar) | Clarity Value After Test* (days aged at ambient) | Notes on Bar |
|---|---|---|
| 1 | — | — |
| 1 (repeat) | 3 (10) | Brittle; minor softening/sticky (fingerprints) |
| 3 | 5 (10) | Oily, completely brittle, opaque |
| 4a | 3 (29) | Very brittle, oily, sticky |
| 4b | 2 (29) | Very brittle, sticky |
| 4c | 1.5 (29) | Very brittle, very oily/sticky |
| DINP ctrl, ex. 1 | 1 (10) | Flexible |
| DINP ctrl, ex. 3 | 1.5 (10) | Very flexible |
| DINP ctrl, ex. 4 | 1 (29) | OK flex/somewhat stiff |

*1-5 scale, 1 = no distortion, 5 = completely opaque. Bars did not exhibit oiliness, stickiness, or inhomogeneity unless noted.

C./min. After equilibration, a dynamic experiment was performed at one frequency using the following conditions: 3° C./min heating rate, 1 Hz frequency, 20 micrometer amplitude, 0.01 pre-load force, force track 120%. Two or three bars of each sample were typically analyzed; in the absence of other factors indicating data quality, numerical data was taken from the bar showing the lowest $T_g$ onset. Glass transition onset values were obtained by extrapolation of the tan delta curve from the first deviation from linearity. The DMTA measurement gives storage modulus (elastic response modulus) and loss modulus (viscous response modulus); the ratio of loss to storage moduli at a given temperature is tan delta. The beginning (onset) of the $T_g$ (temperature of brittle-ductile transition) was obtained for each sample by extrapolating a tangent from the steep inflection of the tan delta curve and the first deviation of linearity from the baseline prior to the beginning of the peak. Table 8 provides a number of DMTA parameters for neat PVC and PVC bars plasticized with triglyceride esters: $T_g$ onset (taken from tan delta); peak of the tan delta curve; storage modulus at 25° C.; and the temperature at which the storage modulus equals 100 MPa (this temperature was chosen to provide an arbitrary measure of the temperature at which the PVC loses a set amount of rigidity; too much loss of rigidity may lead to processing complications for the PVC material). The flexible use temperature range of the plasticized PVC samples is evaluated as the range between the $T_g$ onset and the temperature at which the storage modulus was 100 MPa. A lowering and broadening of the glass transition for neat PVC is observed upon addition of the experimental plasticizers, indicating plasticization and extension of the flexible temperature range of use for neat PVC. Plasticization (enhanced flexibility) is also demonstrated by lowering of the PVC room temperature storage modulus. The data in Table 8 indicate that the neo $C_7$ triglyceride effectively plasticizes PVC and, in fact, provides a wider flexible use temperature range than both DINP and the Oxo $C_7$ triglyceride.

TABLE 8

Various DMTA Thermal Parameters for Plasticized PVC Bars

| Example No. (Plasticizer Used in Bar) | Tan Δ $T_g$ Onset (° C.) | Tan Δ Peak (° C.) | 25° C. Storage Mod. (MPa) | Temp. of 100 MPa Storage Mod. (° C.) | Flexible Use Range (° C.)[a] |
|---|---|---|---|---|---|
| None (neat PVC) | 44.0 | 61.1 | 1433 | 57.1 | 13.1 |
| 1 | −38.6 | 36.5 | 176 | 30.1 | 68.7 |
| 1 (repeat) | — | — | — | — | — |
| 3 | — | — | — | — | — |
| 4a | — | — | — | — | — |
| 4b | — | — | — | — | — |
| 4c | — | — | — | — | — |
| DINP | −37.6 | 17.1 | 48.6 | 16.9 | 54.5 |

— Data not obtained.
[a]Difference between temperature of 100 MPa storage modulus and onset of $T_g$.

Example 12

Demonstration of Plasticization of PVC with Mixed Triglyceride Esters via Dynamic Mechanical Thermal Analysis (DMTA)

Three-point bend Dynamic Mechanical Thermal Analysis (DMTA) with a TA Instruments DMA Q980 fitted with a liquid $N_2$ cooling accessory and a three-point bend clamp assembly was used to measure the thermo-mechanical performance of neat PVC and the PVC/plasticizer blend sample bars prepared in Example 7. Samples were loaded at room temperature and cooled to −60° C. at a cooling rate of 3°

Figure 4:
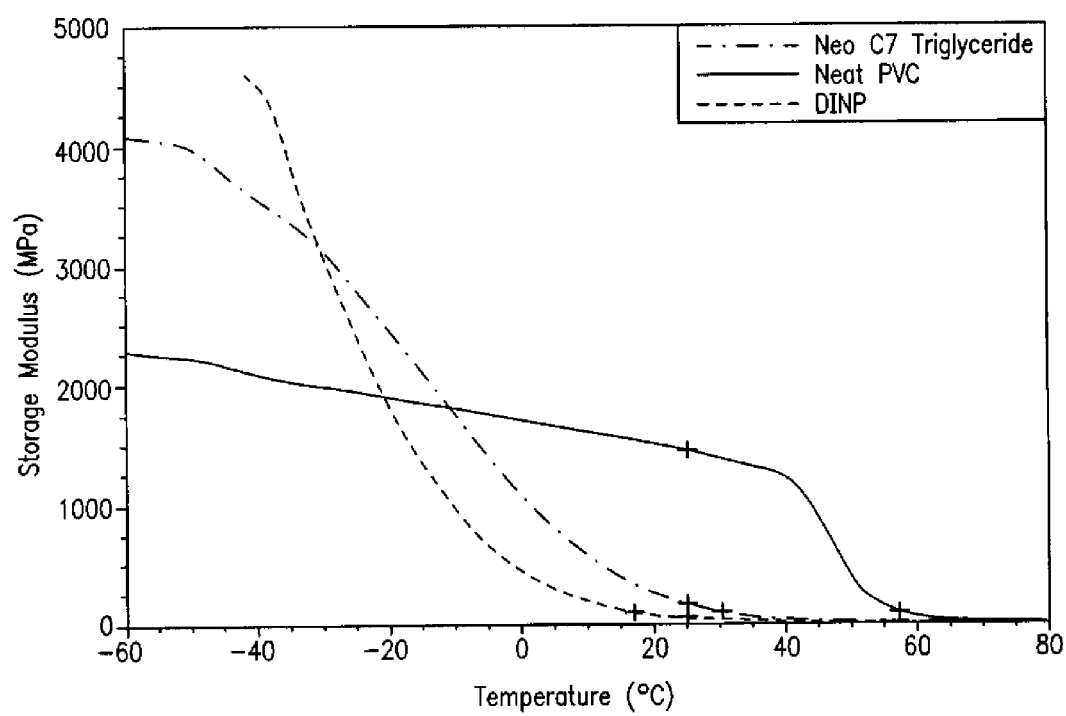
FIG. 4 is an overlay plot of the Dynamic Mechanical Thermal Analysis (DMTA) storage modulus curves for (a) neat PVC, (b) PVC plasticized with the commercial phthalate DINP, and (c) PVC plasticized with the Neo $C_7$ triglyceride ester prepared in Example 1. The cross points marked on the curves indicate the points at which the numerical data given in Table 8 was obtained (temperature of 100 MPa storage modulus, and storage modulus at 25° C.).

FIG. 4 is an overlay plot of the Dynamic Mechanical Thermal Analysis (DMTA) storage modulus curves for (a) neat PVC, (b) PVC plasticized with the commercial phthalate DINP, and (c) PVC plasticized with the Neo $C_7$ triglyceride ester prepared in Example 1. The cross points marked on the curves indicate the points at which the numerical data given in Table 8 was obtained (temperature of 100 MPa storage modulus, and storage modulus at 25° C.).

Figure 5:
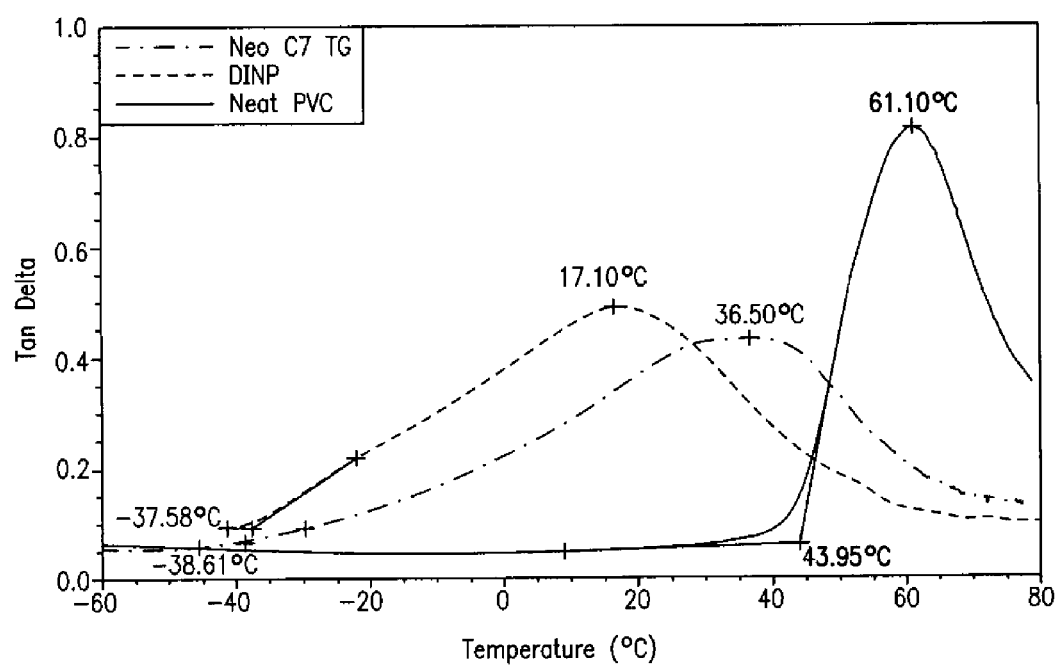
FIG. 5 is an overlay plot of DMTA tan delta curves for (a) neat PVC, (b) PVC plasticized with the commercial phthalate DINP, and (c) PVC plasticized with the Neo $C_7$ triglyceride ester prepared in Example 1. The glass transition onset temperature and tan delta peak temperature (given in Table 8) are labeled for each curve.

FIG. 5 is an overlay plot of DMTA tan delta curves for (a) neat PVC, (b) PVC plasticized with the commercial phthalate DINP, and (c) PVC plasticized with the Neo $C_7$ triglyceride ester prepared in Example 1. The glass transition onset temperature and tan delta peak temperature (given in Table 8) are labeled for each curve.

All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains. The invention has been described above with reference to numerous embodiments and specific examples. Many variations will suggest themselves to those skilled in this art in light of the above detailed description. All such obvious variations are within the full intended scope of the appended claims.

What is claimed is:

1. A plasticizer comprising a triglyceride according to the formula

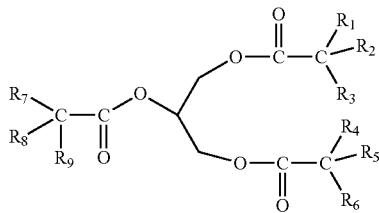

wherein the sum of the carbons for the neoalkyl ester groups, defined as $R^1, R^2, R^3, R^4, R^5, R^6, R^7, R^8, R^9$ plus the 3 carbons for the quaternary carbons bearing $R^1$-$R^9$ and the 3 carbons for the three carbonyl groups, and not including the 3 glycerol backbone carbons, ranges from 20 to 25;
wherein the neoalkyl ester groups, defined as —$C(R^1)(R^2)(R^3)$, —$C(R^4)(R^5)(R^6)$, and —$C(R^7)(R^8)(R^9)$ groups, comprise $C_4$ to $C_{12}$ neoalkyl groups; and
wherein $R^1, R^2, R^3, R^4, R^5, R^6, R^7, R^8$ and $R^9$ comprise $C_1$-$C_9$ alkyl groups.

2. The plasticizer of claim 1, wherein the sum of the carbons for the neoalkyl ester groups ranges from 20 to 24.

3. The plasticizer of claim 1, wherein the sum of the carbons for the neoalkyl ester groups ranges from 21 to 23.

4. The plasticizer of claim 1, wherein the sum of the carbons for the neoalkyl ester groups ranges from 21 to 22.

5. The plasticizer of claim 1, wherein the sum of the carbons for the neoalkyl ester groups is 21.

6. The plasticizer of claim 5, wherein the neoalkyl groups comprise two $C_5$ neoalkyl groups and one $C_8$ neoalkyl group.

7. The plasticizer of claim 5, wherein the neoalkyl groups comprise three $C_6$ neoalkyl groups.

8. The plasticizer of claim 5, wherein the neoalkyl groups comprise one $C_4$, one $C_6$ and one $C_8$ neoalkyl group.

9. The plasticizer of claim 7, wherein the three $C_6$ neoalkyl groups comprise dimethylbutyl, trimethylpropyl, ethylmethylpropyl or combinations thereof.

10. The plasticizer of claim 1, wherein the average branching of the $C_4$ to $C_{12}$ neoalkyl groups is from 2.0 to 3.0 branches per group.

11. The plasticizer of claim 1, wherein the triglyceride comprises greater than or equal to 45 wt % of the plasticizer.

12. The plasticizer of claim 1, wherein the triglyceride comprises greater than or equal to 70 wt % of the plasticizer.

13. The plasticizer of claim 1, wherein the triglyceride comprises greater than or equal to 95 wt % of the plasticizer.

14. The plasticizer of claim 1 characterized as being phthalate-free.

15. A process for producing a neoalkylester plasticizer comprising:
(i) drying a polyol feedstream;
(ii) contacting the dried polyol feedstream with a CO recycle inerts purge stream to absorb $BF_3$;
(iii) pressurizing to 1500 to 2500 psig the contacted dried polyol feedstream, a branched olefin feedstream and a CO feedstream;
(iv) combining the pressurized contacted dried polyol feedstream, the branched olefin feed stream and the CO feedstream in a reactor;
(v) maintaining the reactor at a temperature of 20 to 80° C. for an effective amount of time to form a reactor effluent stream;
(vi) flashing off $BF_3$ and unreacted CO from the reactor effluent stream after the reactor to form a flashed reactor effluent stream;
(vii) heating the flashed reactor effluent stream to remove unreacted branched olefin to form a crude neoalkylester plasticizer; and
(viii) removing residual polyol, oligomers or other impurities from the crude neoester plasticizer to form a neoalkylester plasticizer, wherein the neoalkylester plasticizer is a triglyceride according to the formula

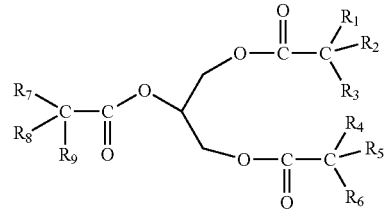

wherein the sum of the carbons for the neoalkyl ester groups, defined as $R^1, R^2, R^3, R^4, R^5, R^6, R^7, R^8, R^9$ plus the 3 carbons for the quaternary carbons bearing $R^1$-$R^9$ and the 3 carbons for the three carbonyl groups, and not including the 3 glycerol backbone carbons, ranges from 20 to 25;
wherein the neoalkyl ester groups, defined as —$C(R^1)(R^2)(R^3)$, —$C(R^4)(R^5)(R^6)$, and —$C(R^7)(R^8)(R^9)$ groups, comprise $C_4$ to $C_{12}$ neoalkyl groups; and
wherein $R^1, R^2, R^3, R^4, R^5, R^6, R^7, R^8, R^9$ comprise $C_1$-$C_9$ alkyl groups.

16. The process of claim 15, wherein the polyol is chosen from ethylene glycol, poly(ethylene glycol), glycerol, pentaerythritol, trimethylol propane, propylene glycol, polypropylene glycol), triethylene glycol, triethylene glycol derivatives, and combinations thereof.

17. The process of claim 15, wherein the drying of the polyol stream step occurs in a distillation column.

18. The process of claim 15 further including stripping residual $BF_3$ from the reactor effluent stream with the CO recycle inerts purge stream prior to step (ii).

19. The process of claim 15 wherein the flashing off step occurs in a high pressure flash drum at 100 to 200 psig to remove $BF_3$ and unreacted excess CO.

20. The process of claim 15 further including recycling the $BF_3$, unreacted CO and olefin back to the suction side of a CO feed compressor.

21. The process of claim 20 wherein the heating the flashed reactor effluent stream step occurs in a flash drum or a falling film evaporator at an effective temperature and pressure.

22. The process of claim 21 further including recycling the unreacted branched olefin back to the reactor.

23. The process of claim 22 wherein the removing residual polyol, oligomers or other impurities occurs in a falling film or a short path evaporator.

24. A process for producing a neoalkylester plasticizer comprising:
(i) contacting a crude glycerol or purified polyol feedstream with a neoacid feedstream in a reactor under effective temperature, pressure and time to form a neoalkylester plasticizer effluent stream, and
(ii) purifying the neoalkylester plasticizer effluent stream to remove unreacted polyol, unreacted neoacid, and other impurities to form a neoalkylester plasticizer, wherein the neoalkylester plasticizer is a triglyceride according to the formula

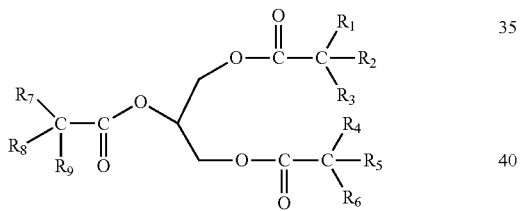

wherein the sum of the carbons for the neoalkyl ester groups, defined as $R^1, R^2, R^3, R^4, R^5, R^6, R^7, R^8, R^9$ plus the 3 carbons for the quaternary carbons bearing $R^1$-$R^9$ and the 3 carbons for the three carbonyl groups, and not including the 3 glycerol backbone carbons, ranges from 20 to 25;
wherein the neoalkyl ester groups, defined as —$C(R^1)(R^2)(R^3)$, —$C(R^4)(R^5)(R^6)$, and —$C(R^7)(R^8)(R^9)$, comprise $C_4$ to $C_{12}$ neoalkyl groups; and
wherein $R^1, R^2, R^3, R^4, R^5, R^6, R^7, R^8, R^9$ comprise $C_1$-$C_9$ alkyl groups.

25. The process of claim 24, wherein the crude glycerol feedstream includes REG, EIS-739, EIS-740, EIS-733, EIS-724, EIS 56-81-5, IRE and mixtures thereof.

26. A process for producing a neoalkylester plasticizer comprising:
(i) drying a polyol feedstream;
(ii) contacting in a reactor the dried polyol feedstream with a neoacid feedstream under effective temperature, pressure and time to form a neoalkylester plasticizer effluent stream, and
(iii) purifying the neoalkylester plasticizer effluent stream to remove unreacted polyol and unreacted neoacid to form a neoalkylester plasticizer, wherein the neoalkylester plasticizer is a triglyceride according to the formula

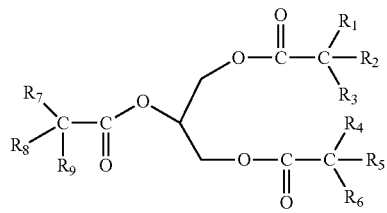

wherein the sum of the carbons for the neoalkyl ester groups, defined as $R^1, R^2, R^3, R^4, R^5, R^6, R^7, R^8, R^9$ plus the 3 carbons for the quaternary carbons bearing $R^1$-$R^9$ and the 3 carbons for the three carbonyl groups, and not including the 3 glycerol backbone carbons, ranges from 20 to 25;
wherein the neoalkyl ester groups, defined as —$C(R^1)(R^2)(R^3)$, —$C(R^4)(R^5)(R^6)$, and —$C(R^7)(R^8)(R^9)$, groups, comprise $C_4$ to $C_{12}$ neoalkyl groups; and
wherein $R^1, R^2, R^3, R^4, R^5, R^6, R^7, R^8, R^9$ comprise $C_1$-$C_9$ alkyl groups.

27. The process of claim 26, wherein the unreacted polyol and unreacted neoacid are recycled back to the reactor.

28. The process of claim 26 wherein the contacting under effective temperature is from 20 to 250° C.

29. The process of claim 26 wherein the contacting under effective pressure is from 1 to 760 mm Hg.

30. The process of claim 26 wherein the contacting under effective time is from 1 to 24 hours.

31. A plasticizer comprising a triglyceride according to the formula

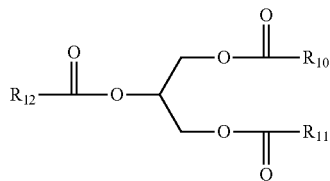

wherein $R_{10}$, $R_{11}$ and $R_{12}$ comprise an aryl group, neoalkyl group or combinations thereof, wherein the sum of the carbons for the aryl or neoalkyl groups plus the 3 carbons for the three carbonyl groups, and not including the 3 glycerol backbone carbons ranges from 20 to 25; and
wherein the branching of the neoalkyl groups is from 2.0 to 3.0 branches per group.

32. The plasticizer of claim 31, wherein the aryl group is selected from a benzoate group, a toluate group and combinations thereof.

33. The plasticizer of claim 32, wherein the toluate group includes the ortho isomer, the meta isomer, the para isomer, and combinations thereof.

34. The plasticizer of claim 31 wherein the molar ratio of the aryl groups to neoalkyl groups ranges from 1:1 to 0.25:4.

* * * * *